United States Patent
Huang et al.

(10) Patent No.: US 8,921,591 B2
(45) Date of Patent: Dec. 30, 2014

(54) PROCESS FOR SYNTHESIZING PHENYLACETIC ACID BY CARBONYLATION OF TOLUENE

(71) Applicant: Lanzhou Institute of Chemical Physics, Chinese Academy of Sciences, Lanzhou (CN)

(72) Inventors: Hanmin Huang, Lanzhou (CN); Chungu Xia, Lanzhou (CN); Pan Xie, Lanzhou (CN)

(73) Assignee: Lanzhou Institute of Chemical Physics, Chinese Academy of Sciences, Lanzhou (CN)

( * ) Notice: Subject to any disclaimer, the term of this patent is extended or adjusted under 35 U.S.C. 154(b) by 0 days.

(21) Appl. No.: 13/722,178

(22) Filed: Dec. 20, 2012

(65) Prior Publication Data

US 2013/0303798 A1    Nov. 14, 2013

(30) Foreign Application Priority Data

May 9, 2012  (CN) .......................... 2012 1 0142005

(51) Int. Cl.
  *C07C 67/36*  (2006.01)
  *C07C 51/09*  (2006.01)

(52) U.S. Cl.
  CPC ................. *C07C 67/36* (2013.01); *C07C 51/09* (2013.01)
  USPC .......................................................... 560/56

(58) Field of Classification Search
  None
  See application file for complete search history.

(56) References Cited

U.S. PATENT DOCUMENTS

| | | | |
|---|---|---|---|
| 5,606,095 A | 2/1997 | Pfiffner et al. | |
| 6,531,597 B2 | 3/2003 | Hoffmann-Emery et al. | |
| 6,653,502 B2 * | 11/2003 | Geissler ........................... | 560/97 |
| 8,664,424 B2 | 3/2014 | Wang et al. | |

FOREIGN PATENT DOCUMENTS

| | | |
|---|---|---|
| CN | 85 1 00362 A | 7/1986 |
| CN | 1039241 A | 1/1990 |
| CN | 1054584 A | 9/1991 |
| CN | 1093355 A | 10/1994 |
| CN | 1109871 A | 10/1995 |
| CN | 1110677 A | 10/1995 |
| CN | 1284406 A | 2/2001 |
| CN | 1491200 A | 4/2004 |
| CN | 101450895 A | 6/2009 |
| CN | 101716523 A | 6/2010 |
| CN | 101816952 A | 9/2010 |
| CN | 102140062 A | 8/2011 |
| JP | 2002249461 A * | 9/2002 |

OTHER PUBLICATIONS

Xie et al. J. Am. Chem. Soc. 2012, 134, 9902-9905.*
Khurana et al. Org. Prep. Proc. Intern. 1994, 580-583.*
Lyons et al. Chem. Rev. 2010, 110, 1147-1169.*
npl-translation-461 (machine translation JP-461).*
Official Action from State Intellectual Property Office of China, dated Jul. 29, 2014, for Patent Application No. 201210142005.9, with English translation, 8 pages.

* cited by examiner

*Primary Examiner* — Brandon Fetterolf
*Assistant Examiner* — Ana Z Muresan
(74) *Attorney, Agent, or Firm* — Seed IP Law Group PLLC

(57) ABSTRACT

A production process for substituted phenylacetic acids or ester analogs thereof is disclosed. In this process toluene or toluene substituted with various substituents, an alcohol, an oxidant and carbon monoxide are used as raw materials to obtain compounds comprising structure of phenylacetic acid ester or analogs thereof by catalysis of the complex catalyst formed from transition metal and ligand, and such compounds are hydrolyzed to obtain various substituted phenylacetic acid based compounds. This type of compounds and their derivatives serve as important fine chemicals used widely in the industries of pharmaceuticals, pesticides, perfume and the like.

19 Claims, No Drawings

PROCESS FOR SYNTHESIZING PHENYLACETIC ACID BY CARBONYLATION OF TOLUENE

FIELD OF ART

The invention is related to a process for preparing compounds comprising structure of phenylacetic acid esters or analogues thereof and substituted phenylacetic acid based compounds, specifically, a process in which toluene or toluene substituted with various substituents, an oxidant, carbon monoxide and an alcohol are used as raw materials to obtain compounds comprising structure of phenylacetic acid esters or analogues thereof via catalysis by a complex catalyst formed from a transition metal and a ligand. Various substituted phenylacetic acid based compounds can be obtained by hydrolysis of such compounds.

BACKGROUND

As an important fine chemical, phenylacetic acid is used widely in the industries of pesticide, pharmaceuticals, perfume or the like.

In the pharmaceuticals industry, phenylacetic acid is converted to sodium salt, potassium salt or other derivatives of phenylacetic acid, such as low toxic precursor phenylacetyl ethanolamine as the precursor of fermentation for producing penicillin to prepare penicillin G. In addition, phenylacetic acid can be converted by chlorination under various conditions to intermediates such as α-chlorophenylacetic acid, p-chlorophenylacetic acid, o-chlorophenylacetic acid, trichlorophenylacetic acid and phenylacetyl chloride etc. p-Chlorophenylacetic acid can be used for producing Azeptin, a medicine developed by Asta-Werke AG, Germany for treating diseases such as bronchial asthma, allergic rhinitis and the like. o-Chlorophenylacetic acid can be used for producing diclofenac sodium, which is a potent anti-inflammatory analgesic medicine. Testosterone phenylacetate, a gonadal hormone, can be produced by reacting phenylacetyl chloride with testosterone. Phenylacetyl chloride can also be used for the synthesis of lorcamide hydrochloride (Lopantrol), which is a novel anti ventricular arrhythmia medicine and has local anesthetic effect. Nitrification of phenylacetic acid under various conditions can produce p-nitrophenylacetic acid, o-nitrophenylacetic acid, m-nitrophenylacetic acid and 2,4-dinitrophenylacetic acid, respectively. p-Nitrophenylacetic acid can be used to produce analgesic and antipyretic medicines such as biphenylacetic acid, pirprofen, ketoprofen, etc. and novel antirheumatic medicine Acrarit with an immunoregulatory effect. 2,4-Dinitrophenylacetic acid can be used in the synthesis of p-aminosalicylic acid, and the latter is a key raw material in the synthesis of the antitubercular medicine sodium para-aminosalicylate PAS-Na. By using phenylacetic acid, phthalic anhydride as raw materials, o-phenylethyl benzene carboxylic acid can be produced by condensation, hydrolysis, hydrogenation, and then neutralization with an acid, and an intermediate benzocycloheptadienone can be further produced, which is a key raw material in the synthesis of tricyclic antidepressant amitriptyline, nortriptyline and antihistaminic agent cyproheptadine. Dibazol, which is used for treating diseases such as mild hypertension and hypertension complicating with coronary heart disease, etc. can be produced by condensation of phenylacetic acid and o-phenylenediamine. Phenylacetic acid also can be used to synthesize benzodiazepine-based derivatives such as estazolam, diazepam, nitrazepam, fludiazapam and the like, which have been developed just since 1980s, and have better therapeutic effect and higher reliability than barbiturates, and are antianxiety drugs which are developed relatively fast, the most widely used and have excellent therapeutic effects. In addition, phenylacetic acid is also widely used in preparation and synthesis of antiepileptic drugs, antidepressant, cardiovascular drugs and antirheumatic drugs.

In the pesticide industry, it is mainly used in the production of insecticides, bactericides, herbicides, rodenticides and the like. For example, the halogenated derivatives of phenylacetic acid, such as α-chlorophenylacetic acid or α-bromophenylacetic acid, the esterified products thereof can be used to synthesize ethyl phenthoate, a non-systemic organophosphorus pesticide and acaricide, which is especially potent for killing coccid. 2,4,6-Trichlorophenylacetic acid is usually prepared in the form of sodium salt aqueous solution commonly known as "fenac", used as a herbicide for the plantations of maize, sugarcane or the like. Phenylacetyl chloride can be used to synthesize N-acylalanine-based systemic bactericide, i.e. benalaxyl, which has good properties, and three characters of low botanic toxicity index, special mechanism of action, and high activity. Phenylacetyl chloride is also widely used as a raw material for a potent rodenticide, i.e. anticoagulant rodenticide, which essentially comprises commercially available products such as Talon, Ratak, Starm, LM-2219 and the like. A phenylacetic acid derivative, phenylacetone can be used to synthesize agropesticide, and it can further be used to produce indanedione-based rodenticides, such as diphacinone sodium salt, chlorophacinone and the like. A derivative of phenylacetic acid, o-nitrophenylacetic acid, can be used to synthesize good herbicides.

In the perfume industry, various phenylacetate ester compounds can be synthesized from phenylacetic acid by esterification, which are used as perfume fixative and modifier in the perfume (essence) industry, and widely used in the industries of soap, detergent, cleanser, cosmetics, tobacco, food, etc.

Phenylacetic acid is a very important fine chemical raw material and many products can be derived therefrom. In recent years, the demand for phenylacetic acid further increases, along with the developments of industries of pharmaceuticals, pesticide, and perfume.

At present, there are dozens of routes for the synthesis of phenylacetic acid. The followings are commonly used: sodium cyanide process, styrene process, acetophenone process and benzyl halide carbonylation process.

Currently, the sodium cyanide process is the most widely used process in China. Although this process is simple and the condition is mild, and can co-produce benzyl cyanide, this process has a higher cost, and the raw material sodium cyanide is highly toxic, with poor safety and tremendous influence on the environment, resulting in severe pollution and requiring higher cost to clean the environment, and therefore the application of this process is limited.

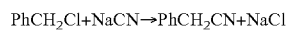
$PhCH_2Cl+NaCN \rightarrow PhCH_2CN+NaCl$

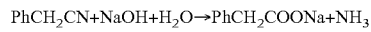
$PhCH_2CN+NaOH+H_2O \rightarrow PhCH_2COONa+NH_3$

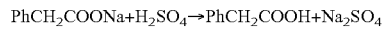
$PhCH_2COONa+H_2SO_4 \rightarrow PhCH_2COOH+Na_2SO_4$

Currently the carbonylation process of benzyl halide is more popular. This process selects benzyl halide and carbon monoxide as raw materials, and obtains phenylacetic acid by a transition metal catalyzed process.

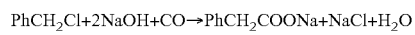
$PhCH_2Cl+2NaOH+CO \rightarrow PhCH_2COONa+NaCl+H_2O$

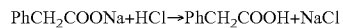
$PhCH_2COONa+HCl \rightarrow PhCH_2COOH+NaCl$

This process was first industrially developed by Dynamit Nobel AG, Germany, and then in other countries some industrial plants were set up. In China, the research in this process began in the late 1980s, and since 1990s some manufacturing plants were set up. Because the raw materials in this process are easy to obtain and the cost is relative low, it was widely investigated (CN1039241, CN1054584, CN1093355, CN1110677, CN1109871, CN1284406, CN85100362, CN101716523A, CN101816952A, etc.). After many years of development, the process is already a mature process and can be performed at lower pressure and lower temperature. However, in this process benzyl halide is used as a raw material, and a large amount of acidic waste is produced in the reaction, therefore plenty of base is needed, which results in a low economical efficiency and more influences on the environment, thus limits the application of the process, and the cost of production is relative high.

Accordingly, it is especially important to use some environmental friendly materials and to provide an environmental friendly process for producing phenylacetic acid based compound.

DISCLOSURE OF THE INVENTION

Toluene is one of the major components of petroleum, and coal tar light oil comprises 15-20% of toluene. Currently, toluene is used in large amount as solvent and high-octane petrol additive, also serves as an important raw material in organic chemical industry. However, compared with benzene and xylene obtained from coal and petroleum, the current production of toluene is relatively in excess.

Accordingly, the object of the present invention is, by adding toluene into a carbonylation reaction system and using a more environmental friendly production process, to obtain substituted phenylacetic acids and ester derivatives thereof with high efficiency, so as to overcome the deficiency of the process in the art.

To achieve the above object, the present invention provides a process for preparing compounds comprising structure of phenylacetic acid esters or analogues thereof and substituted phenylacetic acid based compounds (hereinafter sometimes referred to as "process of the invention"), wherein an aromatic compound substituted with methyl group, an oxidant, an alcohol and carbon monoxide are used as raw materials to synthesize a compound comprising structure of phenylacetic acid esters or analogues thereof in one step by a carbonylation reaction catalyzed by a transition metal, and then a substituted phenylacetic acid based compound is obtained by alkaline hydrolysis. The process of the invention is performed specifically according to the process shown by the following general scheme:

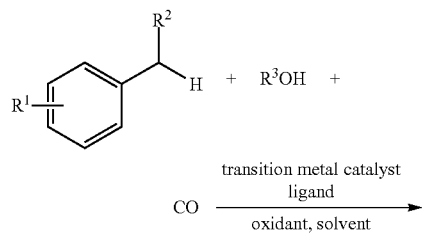

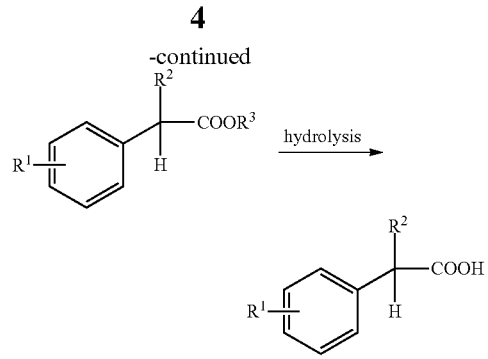

wherein
$R^1$ and $R^2$ groups are each independently selected from: hydrogen, linear or branched $C_1$-$C_{40}$ hydrocarbyl, preferably $C_1$-$C_{30}$ hydrocarbyl, more preferably $C_1$-$C_{20}$ aliphatic hydrocarbyl, most preferably linear or branched $C_{1-4}$ alkyl, examples thereof including methyl, ethyl, propyl, isopropyl, butyl, isobutyl and the like; substituted or unsubstituted $C_6$-$C_{60}$, preferably $C_6$-$C_{30}$, more preferably $C_6$-$C_{20}$ aryl group, examples thereof including phenyl, substituted phenyl, benzyl, substituted benzyl, 1-naphthyl, 2-naphthyl, naphthyl substituted with 1-7 substituents which are $C_1$-$C_{40}$ alkyl (preferably $C_1$-$C_{30}$ alkyl, more preferably $C_1$-$C_{20}$ alkyl), $C_1$-$C_{40}$ alkoxy (preferably $C_1$-$C_{30}$ alkoxy, more preferably $C_1$-$C_{20}$ alkoxy), $C_6$-$C_{60}$ (preferably $C_6$-$C_{30}$, more preferably $C_6$-$C_{20}$) aryl group, $C_6$-$C_{60}$ (preferably $C_6$-$C_{30}$, more preferably $C_6$-$C_{20}$) aryloxy or other substituents, and preferred are $C_{1-4}$ alkyl, $C_{1-4}$ alkoxy, phenyl, phenoxy or halogen substituents; linear or branched $C_1$-$C_{40}$ alkoxy, preferably $C_1$-$C_{30}$ alkoxy, more preferably $C_1$-$C_{20}$ alkoxy, and most preferably linear or branched $C_{1-4}$ alkoxy; halogen; furanyl, furanyl substituted with 1-3 substituents which are $C_1$-$C_{40}$ alkyl (preferably $C_1$-$C_{30}$ alkyl, more preferably $C_1$-$C_{20}$ alkyl), $C_1$-$C_{40}$ alkoxy (preferably $C_1$-$C_{30}$ alkoxy, more preferably $C_1$-$C_{20}$ alkoxy), $C_6$-$C_{60}$ (preferably $C_6$-$C_{30}$, more preferably $C_6$-$C_{20}$) aryl, $C_6$-$C_{60}$ (preferably $C_6$-$C_{30}$, more preferably $C_6$-$C_{20}$) aryloxy or other substituents, and preferred are $C_{1-4}$ alkyl, $C_{1-4}$ alkoxy, phenyl, phenoxy or halogen substituents; pyridinyl, pyridinyl substituted with 1-4 substituents which are $C_1$-$C_{40}$ alkyl (preferably $C_1$-$C_{30}$ alkyl, more preferably $C_1$-$C_{20}$ alkyl), $C_1$-$C_{40}$ alkoxy (preferably $C_1$-$C_{30}$ alkyl, more preferably $C_1$-$C_{20}$ alkyl), $C_6$-$C_{60}$ (preferably $C_6$-$C_{30}$, more preferably $C_6$-$C_{20}$) aryl, $C_6$-$C_{60}$ (preferably $C_6$-$C_{30}$, more preferably $C_6$-$C_{20}$) aryloxy or other substituents, and preferred are $C_{1-4}$ alkyl, $C_{1-4}$ alkoxy, phenyl, phenoxy or halogen substituents; hydroxyl; nitro; amino; linear or branched $C_1$-$C_{40}$ ester group, preferably linear or branched $C_1$-$C_6$ ester group; linear or branched $C_1$-$C_{40}$ acyl, preferably linear or branched $C_1$-$C_6$ acyl; sulfonic acid group; $R^3$ is selected from linear or branched $C_1$-$C_{30}$ alkyl, benzyl or substituted benzyl, preferably methyl, ethyl, propyl, isopropyl, butyl or isobutyl.

In a preferred embodiment, $R^1$ and $R^2$ groups are each independently selected from: hydrogen; linear or branched $C_{1-4}$ alkyl, preferably methyl, ethyl, propyl, isopropyl, butyl; linear or branched $C_{1-4}$ alkoxy, preferably methoxy, ethoxy, propoxy, butoxy; phenyl, phenyl substituted with 1-3 substituents which are $C_1$-$C_{40}$ alkyl (preferably $C_1$-$C_{30}$ alkyl, more preferably $C_1$-$C_{20}$ alkyl), $C_1$-$C_{40}$ alkoxy (preferably $C_1$-$C_{30}$ alkoxy, more preferably $C_1$-$C_{20}$ alkoxy), $C_6$-$C_{60}$ (preferably $C_6$-$C_{30}$, more preferably $C_6$-$C_{20}$) aryl, $C_6$-$C_{60}$ (preferably $C_6$-$C_{30}$, more preferably $C_6$-$C_{20}$) aryloxy or other substituents, and preferred are $C_{1-4}$ alkyl, $C_{1-4}$ alkoxy, phenyl, phenoxy or halogen substituents; benzyl, substituted benzyl, 1-naphthyl, 2-naphthyl, naphthyl substituted with 1-3 substituents which are $C_1$-$C_{40}$ alkyl (preferably $C_1$-$C_{30}$ alkyl, more preferably $C_1$-$C_{20}$ alkyl), $C_1$-$C_{40}$ alkoxy (preferably $C_1$-$C_{30}$ alkoxy, more preferably $C_1$-$C_{20}$ alkoxy), $C_6$-$C_{60}$ (preferably $C_6$-$C_{30}$, more preferably $C_6$-$C_{20}$) aryl, $C_6$-$C_{60}$ (preferably $C_6$-$C_{30}$, more preferably $C_6$-$C_{20}$) aryloxy or other substituents, and preferred are $C_{1-4}$ alkyl, $C_{1-4}$ alkoxy, phenyl, phenoxy or halogen substituents; halogen, and examples thereof are fluorine, chlorine, iodine and bromine; furanyl; pyridinyl; $C_1$-$C_6$ aliphatic acyl, benzoyl, thiobenzoyl; hydroxyl, nitro, amino, $C_1$-$C_6$ ester group, $C_1$-$C_6$ aldehyde group; sulfonic acid group. In a preferred embodiment, $R^3$ is selected from the following groups: methyl, ethyl, propyl, isopropyl, butyl, isobutyl, benzyl or benzyl having a benzene ring substituted with 1-5 substituents which are $C_1$-$C_{40}$ alkyl (preferably $C_1$-$C_{30}$ alkyl, more preferably $C_1$-$C_{20}$ alkyl), $C_1$-$C_{40}$ alkoxy (preferably $C_1$-$C_{30}$ alkoxy, more preferably $C_1$-$C_{20}$ alkoxy), $C_6$-$C_{60}$ (preferably $C_6$-$C_{30}$, more preferably $C_6$-$C_{20}$) aryl, $C_6$-$C_{60}$ (preferably $C_6$-$C_{30}$, more preferably $C_6$-$C_{20}$) aryloxy or other substituents, and preferred are $C_{1-4}$ alkyl, $C_{1-4}$ alkoxy, phenyl, phenoxy, or halogen substituents.

It should be noted that, unless specially indicated in the context, when "substituted" group is mentioned, substituent refers to alkyl, alkoxy, aryl, aryloxy or other substituents whose number of carbon atom does not exceed that of the main chain.

Specifically, the preparation process of the invention includes the following steps: a transition metal catalyst precursor, a ligand, a substituted toluene, an alcohol and an oxidant are added into a reaction kettle containing an organic solvent (80-150° C.), into which carbon monoxide (1-50 atm) is introduced; when the pressure does not decrease any more, the reaction is accomplished, and the reaction solution is subjected to column chromatography or distillation under reduced pressure to obtain the desired compound comprising structure of phenylacetic acid esters or analogues thereof. The compound obtained is subjected to alkaline hydrolysis (pH=10-14) followed by acidification to pH=1, and then extraction with ethyl acetate to obtain the desired substituted phenylacetic acid based compounds.

In the process of the invention, the reaction temperature of carbonylation of toluene is generally controlled between 80 and 150° C., preferably at 120° C.

In the process of the invention, the pressure of carbon monoxide is generally controlled in the range of from 1 to 50 atm, preferably 10 atm.

In the process of the invention, the method of alkaline hydrolysis is not limited and can be any alkaline hydrolysis method commonly used in the art, for example, a reaction in an alkaline solution (e.g. 6 N sodium hydroxide solution, potassium hydroxide solution etc.) at 60° C. for 2 to 4 h.

In the preparation process of the invention, the transition metal catalyst precursor is one or more selected from: ruthenium-based metal catalyst precursors; ruthenium trichloride, dodecacarbonyltriruthenium; rhodium-based metal catalyst precursors, preferably rhodium trichloride, rhodium acetate, dodecacarbonyltetrarhodium, tris(triphenylphosphinecarbonyl) rhodium hydride, triphenylphosphinecarbonyl rhodium acetylacetonate, vinyl rhodium chloride; palladium-based metal catalyst precursors, preferably palladium chloride, palladium on carbon, tetra(triphenylphosphine) palladium, di(triphenylphosphine) palladium dichloride, palladium acetate, palladium trifluoroacetate, benzonitrile palladium dichloride, acetonitrile palladium dichloride and palladium trifluoromethanesulfonate; iridium-based metal catalyst precursors, preferably iridium trichloride; cobalt-based metal catalyst precursors, preferably carbonyl cobalt, cobalt chloride, cobalt bromide and cobalt acetylacetonate; nickel-based metal catalyst precursors, preferably nickel bromide, nickel acetate, nickel sulfate, nickel acetylacetonate and nickel chloride; copper-based metal catalyst precursors, preferably copper fluoride, copper chloride, copper acetylacetonate. Preferable transition metal catalyst precursor is palladium chloride.

In the preparation process of the invention, the oxidant is one or more selected from: peroxide oxidants, preferably di-tert-butyl peroxide, tert-butyl hydroperoxide, hydrogen peroxide, peroxyacetic acid, m-chloroperoxybenzoic acid, diisopropylbenzene peroxide, benzoyl peroxide and bis(tert-butylperoxy)diisopropylbenzene; quinone type oxidants, preferably p-benzoquinone, anthraquinone, tetrachlorobenzoquinone, tetramethyl-p-benzoquinone and dichlorodicyanobenzoquinone; fluorine type oxidants, preferably N-fluorodibenzenesulfonamide, N-fluoropyridinium trifluoromethanesulfonate and N-fluoropyridinium tetrafluoroborate; oxygen; persulphates, preferably potassium persulphate, sodium persulphate and potassium hydrogen persulphate. Preferable oxidants are di-tert-butyl peroxide and bis(tert-butylperoxy)diisopropylbenzene.

In the preparation process of the invention, the ligand is one or more selected from: phosphine ligands, preferably Xantphos (4,5-bis(diphenylphosphino)-9,9-dimethylxanthene), BINAP (2,2'-bis(diphenylphosphino)-1,1'-binaphthyl), MeO-BIPHEP (2,2'-bis(diphenylphosphino)-6,6'-dimethoxy-1,1'-biphenyl), $PPh_3$ (triphenylphosphine), DPPF (1,1'-bis(diphenylphosphino)ferrocene) and DPEphos (bis[(2-diphenylphosphino)phenyl]ether); nitrogen ligands, preferably pyridine, 2,2'-bipyridyl, 2,2'-biquinolyl and 1,10-phenanthroline. Preferable ligand is Xantphos (4,5-bis(diphenylphosphino)-9,9-dimethylxanthene).

In the preparation process of the invention, the organic solvent is selected from benzene, nitromethane, toluene, trifluorotoluene, xylene, mesitylene, 1,4-dioxane, acetonitrile, propionitrile, dichloromethane, chloroform, carbon tetrachloride, 1,2-dichloroethane, ethyl ether, glycol dimethyl ether, methyl tert-butyl ether, methyl cyclopentyl ether, tetrahydrofuran, N,N-dimethylformamide, N,N-dimethylacetamide, dimethyl sulfoxide, or mixtures thereof. Preferable organic solvent is benzene.

The present invention has the following advantageous effects:

1. The process of the present invention uses the industrially accessible toluene-based compounds and alcohols as raw materials of the reaction, and under the catalysis of the transition metal catalyst, in a manner of direct carbonylation of $C(sp^3)$—H bond, obtains compounds comprising structure of phenylacetic acid ester or analogues thereof via only one step in high yield, and said compounds can be hydrolyzed to obtain substituted phenylacetic acid based compounds in high yield.

2. The raw materials used in the process of the present invention are simple and can be obtained from a wide range of sources. The catalysts used are relatively cheap, the conditions of the reaction are more moderate, and the production process is better. The phenylacetic acid based compounds obtained can be used widely in industrial fields such as pharmaceuticals, pesticides etc.

3. The substituted phenylacetic acid ester based compounds co-produced by the process of the present invention are also widely used in industries of perfume, food and the like, thus there are important prospects of application in industrial productions.

SPECIFIC EMBODIMENTS

The preparation of the present invention can be further illustrated by the preparation procedures of representative compounds as follows.

Example 1

Preparation of Phenylacetic Acid from Toluene and Methanol

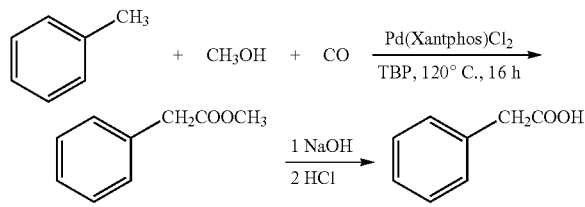

Toluene (1.38 g), methanol (32 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 67 mg methyl phenylacetate was obtained by column chromatography, in a yield of 89%. $^1$HNMR (400 MHz, CDCl$_3$) δ 3.60 (s, 2H), 3.65 (s, 3H), 7.22-7.32 (m, 5H); $^{13}$CNMR (100 MHz, CDCl$_3$) δ 41.2, 52.0, 127.1, 128.6, 129.3, 134.1, 172.0; HRMS (ESI) calcd. for C$_9$H$_{10}$NaO$_2$ [M+Na]: 173.0568. found: 173.0573. The methyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 58 mg product phenylacetic acid was obtained by extraction with ethyl acetate, and the yield of hydrolysis was 95%.

Example 2

Preparation of Phenylacetic Acid from Toluene and Ethanol

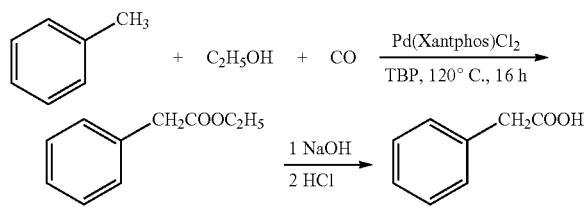

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 76 mg ethyl phenylacetate was obtained by column chromatography, in a yield of 93%. $^1$HNMR (400 MHz, CDCl$_3$) δ 1.23 (t, J=7.2 Hz, 3H), 3.61 (s, 2H), 4.12 (q, J=7.2 Hz, 2H), 7.24-7.35 (m, 5H); $^{13}$CNMR (100 MHz, CDCl$_3$) δ 14.2, 41.5, 60.9, 127.0, 128.6, 129.3, 134.2, 171.6; HRMS (ESI) calcd. for C$_{10}$H$_{12}$NaO$_2$ [M+Na]: 187.0728. found: 187.0730. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 59 mg product phenylacetic acid was obtained by extraction with ethyl acetate, and the yield of hydrolysis was 93%.

Example 3

Preparation of Phenylacetic Acid from Toluene and n-Propanol

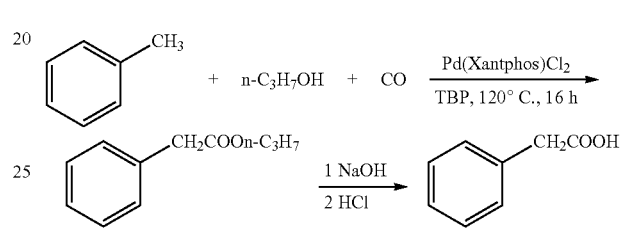

Toluene (1.38 g), n-propanol (60 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 78 mg n-propyl phenylacetate was obtained by column chromatography, in a yield of 88%. $^1$HNMR (400 MHz, CDCl$_3$) δ 0.88 (t, J=7.6 Hz, 3H), 1.59-1.67 (m, 2H), 3.61 (s, 2H), 4.12 (t, J=6.8 Hz, 2H), 7.23-7.33 (m, 5H); $^{13}$CNMR (100 MHz, CDCl$_3$) δ 10.3, 21.9, 41.5, 66.4, 127.0, 129.3, 134.3, 171.7; HRMS (ESI) calcd. for C$_{11}$H$_{14}$NaO$_2$ [M+Na]: 201.0886. found: 201.0886. The n-propyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 56 mg product phenylacetic acid was obtained by extraction with ethyl acetate, and the yield of hydrolysis was 94%.

Example 4

Preparation of Phenylacetic Acid from Toluene and Isopropanol

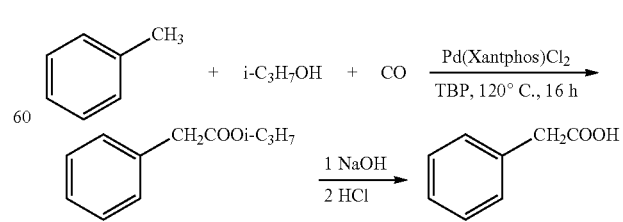

Toluene (1.38 g), isopropanol (60 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 75 mg isopropyl phenylacetate was obtained by column chromatography, in a yield of 84%. $^1$HNMR (400 MHz, CDCl$_3$) δ 1.21 (s, 3H), 1.23 (s, 3H), 3.58 (s, 2H), 4.96-5.06 (m, 1H), 7.23-7.34 (m, 5H); $^{13}$CNMR (100 MHz, CDCl$_3$) δ 21.8, 41.7, 68.2, 126.9, 128.5, 129.2, 134.4, 171.1; HRMS (ESI) calcd. for C$_{11}$H$_{14}$NaO$_2$ [M+Na]: 201.0886. found: 201.0886. The isopropyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 54 mg product phenylacetic acid was obtained by extraction with ethyl acetate, and the yield of hydrolysis was 94%.

Example 5

Preparation of Phenylacetic Acid from Toluene and n-Butanol

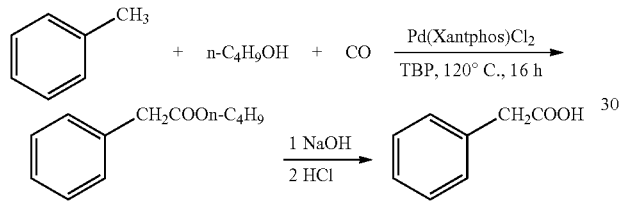

Toluene (1.38 g), n-butanol (74 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 65 mg n-butyl phenylacetate was obtained by column chromatography, in a yield of 68%. $^1$HNMR (400 MHz, CDCl$_3$) δ 0.88 (t, J=7.6 Hz, 3H), 1.29-1.38 (m, 2H), 1.55-1.62 (m, 2H), 3.60 (s, 2H), 4.06 (t, J=6.8 Hz, 2H), 7.23-7.33 (m, 5H); $^{13}$CNMR (100 MHz, CDCl$_3$) δ 13.7, 19.1, 30.6, 41.5, 64.7, 127.0, 128.5, 129.3, 134.3, 171.7; HRMS (ESI) calcd. for C$_{12}$H$_{16}$NaO$_2$ [M+Na]: 215.1043. found: 215.1042. The n-butyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 43 mg product phenylacetic acid was obtained by extraction with ethyl acetate, and the yield of hydrolysis was 94%.

Example 6

Preparation of Phenylacetic Acid from Toluene and Isobutanol

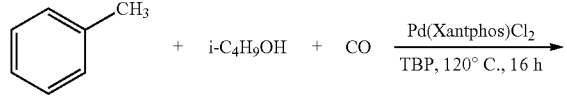

-continued

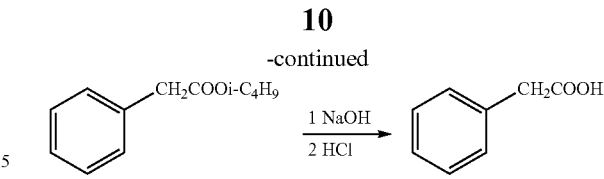

Toluene (1.38 g), isobutanol (74 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 69 mg isobutyl phenylacetate was obtained by column chromatography, in a yield of 72%. $^1$HNMR (400 MHz, CDCl$_3$) δ 0.88 (s, 3H), 0.89 (s, 3H), 1.85-1.96 (m, 1H), 3.62 (s, 2H), 3.86 (d, J=6.8 Hz, 1H), 7.23-7.34 (m, 5H); $^{13}$CNMR (100 MHz, CDCl$_3$) δ 19.0, 27.7, 41.5, 70.9, 127.0, 128.5, 129.3, 134.3, 171.6; HRMS (ESI) calcd. for C$_{12}$H$_{16}$NaO$_2$ [M+Na]: 215.1043. found: 215.1037. The isobutyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 53 mg product phenylacetic acid was obtained by extraction with ethyl acetate, and the yield of hydrolysis was 93%.

Example 7

Preparation of Phenylacetic Acid from Toluene and Tert-Butanol

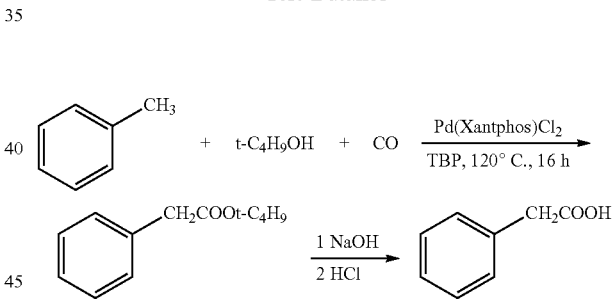

Toluene (1.38 g), tert-butanol (74 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 53 mg tert-butyl phenylacetate was obtained by column chromatography, in a yield of 58%. $^1$HNMR (400 MHz, CDCl$_3$) δ 1.43 (s, 9H), 3.51 (s, 2H), 7.21-7.31 (m, 5H); $^{13}$CNMR (100 MHz, CDCl$_3$) δ 28.1, 42.7, 80.8, 126.9, 128.6, 129.2, 134.8, 170.9; HRMS (ESI) calcd. for C$_{12}$H$_{16}$NaO$_2$ [M+Na]: 215.1043. found: 215.1045. The tert-butyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 36 mg product phenylacetic acid was obtained by extraction with ethyl acetate, and the yield of hydrolysis was 96%.

Example 8

Preparation of o-Methylphenylacetic Acid from o-Xylene and Ethanol

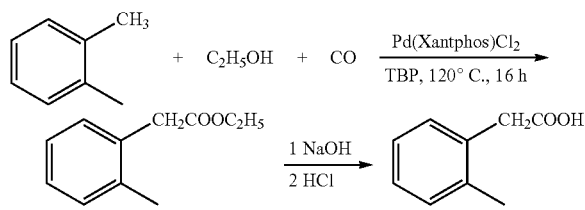

o-Xylene (1.59 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 81 mg ethyl o-methylphenylacetate was obtained by column chromatography, in a yield of 91%. $^1$HNMR (400 MHz, CDCl$_3$) δ 1.23 (t, J=7.2 Hz, 3H), 2.32 (s, 3H), 3.63 (s, 2H), 4.12 (q, J=7.2 Hz, 2H), 7.15-7.21 (m, 4H); $^{13}$CNMR (100 MHz, CDCl$_3$) δ 14.2, 19.6, 39.3, 60.8, 126.1, 127.3, 130.1, 130.3, 132.9, 136.8, 171.5; HRMS (ESI) calcd. for C$_{11}$H$_{14}$NaO$_2$ [M+Na]: 201.0886. found: 201.0882. The ethyl o-methylphenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 66 mg product o-methylphenylacetic acid was obtained by extraction with ethyl acetate, and the yield of hydrolysis was 97%.

Example 9

Preparation of m-Methylphenylacetic Acid from m-Xylene and Ethanol

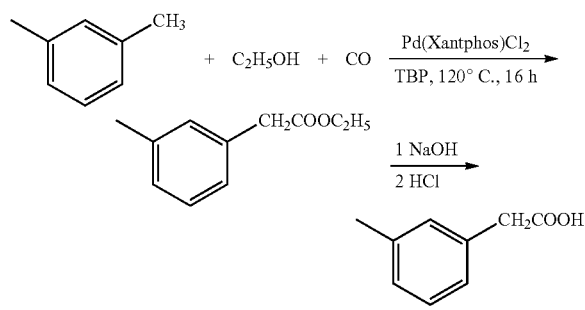

m-Xylene (1.59 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 80 mg ethyl m-methylphenylacetate was obtained by column chromatography, in a yield of 90%. $^1$HNMR (400 MHz, CDCl$_3$) δ 1.23 (t, J=7.2 Hz, 3H), 2.33 (s, 3H), 3.57 (s, 2H), 4.12 (q, J=7.2 Hz, 2H), 7.06-7.09 (m, 3H), 7.19-7.24 (m, 3H); $^{13}$CNMR (100 MHz, CDCl$_3$) δ14.2, 21.4, 41.4, 60.8, 126.3, 127.8, 128.5, 130.0, 134.1, 138.2, 171.8; HRMS (ESI) calcd. for C$_{11}$H$_{14}$NaO$_2$ [M+Na]: 201.0886. found: 201.0887. The ethyl m-methylphenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 63 mg product m-methylphenylacetic acid was obtained by extraction with ethyl acetate, and the yield of hydrolysis was 93%.

Example 10

Preparation of p-Methylphenylacetic Acid from p-Xylene and Ethanol

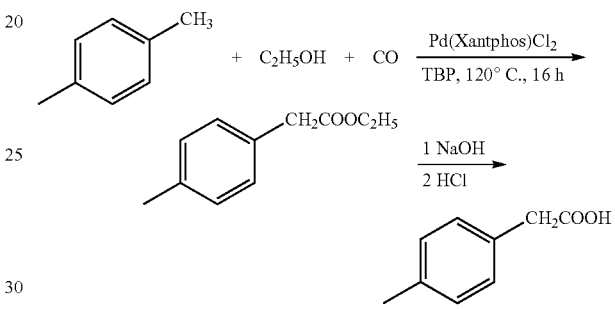

p-Xylene (1.59 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 85 mg ethyl p-methylphenylacetate was obtained by column chromatography, in a yield of 96%. $^1$HNMR (400 MHz, CDCl$_3$) δ 1.23 (t, J=7.2 Hz, 3H), 2.33 (s, 3H), 3.57 (s, 2H), 4.11 (q, J=7.2 Hz, 2H), 7.11-7.18 (m, 4H); $^{13}$CNMR (100 MHz, CDCl$_3$) δ 14.2, 21.1, 41.0, 60.8, 129.1, 139.3, 131.1, 136.6, 171.8; HRMS (ESI) calcd. for C$_{11}$H$_{14}$NaO$_2$ [M+Na]: 201.0886. found: 201.0882. The ethyl p-methylphenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 69 mg product p-methylphenylacetic acid was obtained by extraction with ethyl acetate, and the yield of hydrolysis was 96%.

Example 11

Preparation of p-Methoxyphenylacetic Acid from p-Methoxy Toluene and Ethanol

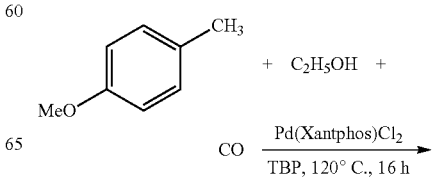

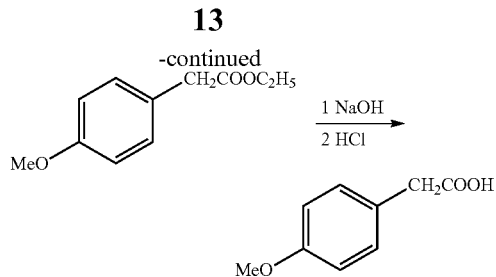

p-Methoxy toluene (1.83 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 82 mg ethyl p-methoxyphenylacetate was obtained by column chromatography, in a yield of 85%. $^1$HNMR (400 MHz, CDCl$_3$) δ 1.23 (t, J=6.8 Hz, 3H), 3.54 (s, 2H), 3.79 (s, 3H), 4.11 (q, J=6.8 Hz, 2H), 6.84-6.88 (m, 2H), 7.18-7.22 (m, 2H); $^{13}$CNMR (100 MHz, CDCl$_3$) δ 14.2, 40.5, 55.3, 60.8, 113.9, 126.3, 130.3, 158.7, 171.9; HRMS (ESI) calcd. for C$_{11}$H$_{14}$NaO$_3$ [M+Na]: 217.0835. found: 217.0838. The ethyl p-methoxyphenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 64 mg product p-methoxyphenylacetic acid was obtained by extraction with ethyl acetate, and the yield of hydrolysis was 91%.

Example 12

Preparation of p-Ethoxyphenylacetic Acid from p-Ethoxy Toluene and Ethanol

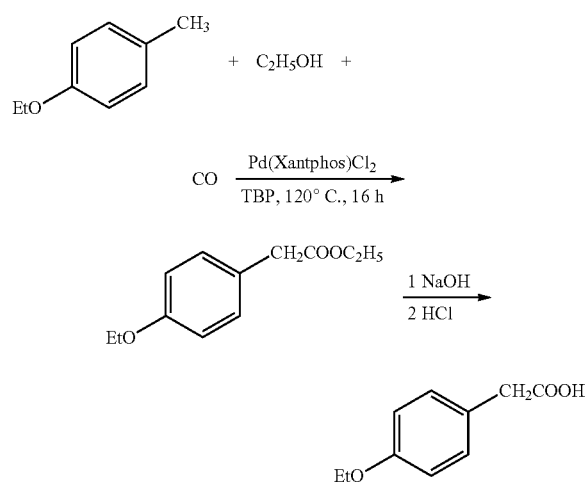

p-Ethoxy toluene (2.04 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 89 mg ethyl p-ethoxyphenylacetate was obtained by column chromatography, in a yield of 86%. $^1$HNMR (400 MHz, CDCl$_3$) δ 1.22 (t, J=7.2 Hz, 3H), 1.38 (t, J=7.2 Hz, 3H), 3.54 (s, 2H), 3.98 (q, J=7.2 Hz, 2H), 4.11 (q, J=6.8 Hz, 2H), 6.83-6.86 (m, 2H), 7.17-7.20 (m, 2H); $^{13}$CNMR (100 MHz, CDCl$_3$) δ 13.2, 13.8, 39.5, 59.7, 69.7, 62.4, 113.5, 125.1, 129.2, 156.9, 170.9; HRMS (ESI) calcd. for C$_{12}$H$_{16}$NaO$_3$ [M+Na]: 231.0992. found: 231.0989. The ethyl p-ethoxyphenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 72 mg product p-ethoxyphenylacetic acid was obtained by extraction with ethyl acetate, and the yield of hydrolysis was 93%.

Example 13

Preparation of 2-(4-n-Propoxyphenyl)Acetic Acid from 4-n-Propoxytoluene and Ethanol

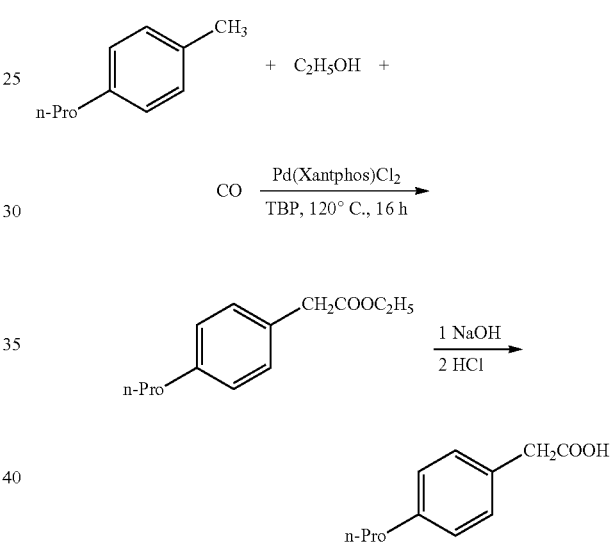

4-n-propoxytoluene (1.8 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 88 mg ethyl 2-(4-n-propoxyphenyl)acetate was obtained by column chromatography, in a yield of 79%. $^1$HNMR (400 MHz, CDCl$_3$) δ 1.00 (t, J=7.6 Hz, 3H), 1.23 (t, J=7.2 Hz, 3H), 1.75-1.84 (m, 2H), 3.54 (s, 2H), 3.88 (t, J=6.4 Hz, 2H), 4.11 (q, J=7.2 Hz, 2H), 6.83-6.87 (m, 2H), 7.16-7.20 (m, 2H); $^{13}$CNMR (100 MHz, CDCl$_3$) δ 10.5, 14.2, 22.6, 40.6, 60.8, 69.5, 114.6, 126.0, 130.2, 158.2, 171.9; HRMS (ESI) calcd. for C$_{13}$H$_{18}$NaO$_3$ [M+Na]: 245.1148. found: 245.1157. The ethyl 2-(4-n-propoxyphenyl)acetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 73 mg product 2-(4-n-propoxyphenyl)acetic acid was obtained by extraction with ethyl acetate, and the yield of hydrolysis was 95%.

Example 14

Preparation of 2-(4-n-Butoxyphenyl)Acetic Acid from 4-n-Butoxytoluene and Ethanol

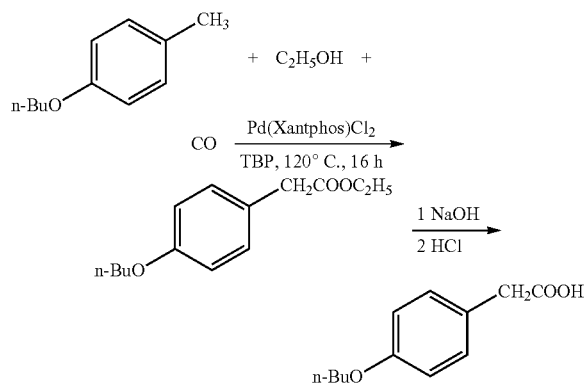

4-n-butoxytoluene (2.46 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 107 mg ethyl 2-(4-n-butoxyphenyl)acetate was obtained by column chromatography, in a yield of 91%. $^1$HNMR (400 MHz, CDCl$_3$) δ 0.95 (t, J=7.6 Hz, 3H), 1.23 (t, J=7.2 Hz, 3H), 1.45-1.53 (m, 2H), 1.72-1.79 (m, 2H), 3.54 (s, 2H), 3.92 (t, J=6.4 Hz, 2H), 4.11 (q, J=7.2 Hz, 2H), 6.83-6.86 (m, 2H), 7.17-7.19 (m, 2H); $^{13}$CNMR (100 MHz, CDCl$_3$) δ 13.9, 14.2, 19.3, 31.3, 40.6, 60.8, 67.7, 114.6, 126.0, 130.2, 158.3, 171.9; HRMS (ESI) calcd. for C$_{14}$H$_{20}$NaO$_3$ [M+Na]: 259.1305. found: 259.1312. The ethyl 2-(4-n-butoxyphenyl) acetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 91 mg product 2-(4-n-butoxyphenyl)acetic acid was obtained by extraction with ethyl acetate, and the yield of hydrolysis was 96%.

Example 15

Preparation of 2-(4-(n-Hexyloxy)Phenyl)Acetic Acid from 4-(n-Hexyloxy)Toluene and Ethanol

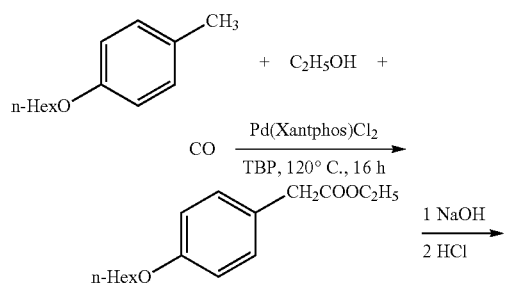

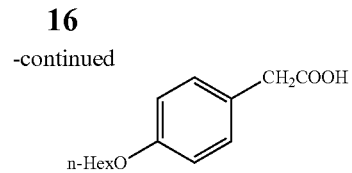

4-(n-hexyloxy)toluene (2.88 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 116 mg ethyl 2-(4-(n-hexyloxy)phenyl) acetate was obtained by column chromatography, in a yield of 88%. $^1$HNMR (400 MHz, CDCl$_3$) δ 0.88 (t, J=7.2 Hz, 3H), 1.23 (t, J=7.2 Hz, 3H), 1.31-1.36 (m, 4H), 1.41-1.46 (m, 2H), 1.73-1.79 (m, 2H), 3.54 (s, 2H), 3.91 (t, J=6.8 Hz, 2H), 4.11 (q, J=7.2 Hz, 2H), 6.83-6.87 (m, 2H), 7.17-7.19 (m, 2H); $^{13}$CNMR (100 MHz, CDCl$_3$) δ 14.0, 14.2, 22.6, 25.7, 29.3, 25.7, 29.3, 31.6, 40.6, 60.8, 68.0, 114.6, 126.0, 130.2, 158.2, 171.9; HRMS (ESI) calcd. for C$_{16}$H$_{24}$NaO$_3$ [M+Na]: 287.1618. found: 287.1622. The ethyl 2-(4-(n-hexyloxy)phenyl)acetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 97 mg product 2-(4-(n-hexyloxy)phenyl)acetic acid was obtained by extraction with ethyl acetate, and the yield of hydrolysis was 94%.

Example 16

Preparation of 3,5-Dimethylphenylacetic Acid from Mesitylene and Ethanol

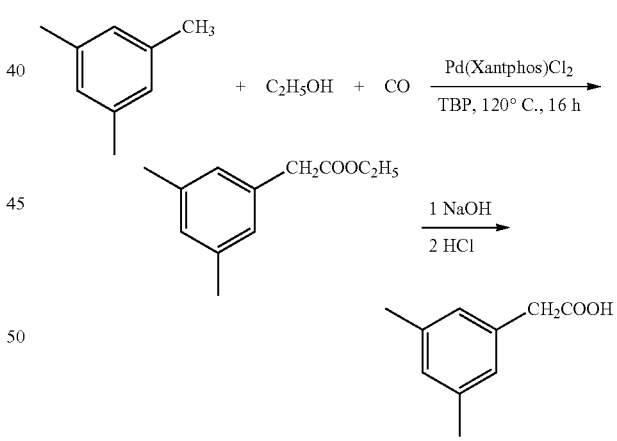

Mesitylene (1.8 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 85 mg ethyl 3,5-dimethylphenylacetate was obtained by column chromatography, in a yield of 89%. $^1$HNMR (400 MHz, CDCl$_3$) δ 1.24 (t, J=7.2 Hz, 3H), 2.30 (s, 6H), 3.53 (s, 2H), 4.12 (q, J=7.2 Hz, 2H), 6.84-6.95 (m, 3H); $^{13}$CNMR (100 MHz, CDCl$_3$) δ 14.2, 21.3, 41.3, 60.8, 127.0, 128.7, 133.9, 138.1, 171.9; HRMS (ESI) calcd. for $C_{12}H_{16}NaO_2$ [M+Na]: 215.1043. found: 215.1040. The ethyl 3,5-dimethylphenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 70 mg product 3,5-dimethylphenylacetic acid was obtained by extraction with ethyl acetate, and the yield of hydrolysis was 96%.

Example 17

Preparation of p-Fluorophenylacetic Acid from p-Fluorotoluene and Ethanol

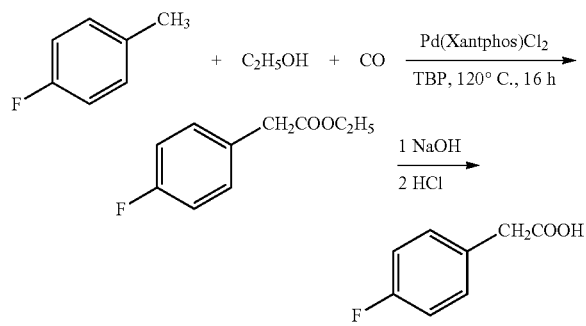

p-Fluorotoluene (1.65 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 76 mg ethyl p-fluorophenylacetate was obtained by column chromatography, in a yield of 84%. $^1$HNMR (400 MHz, CDCl$_3$) δ 1.23 (t, J=7.2 Hz, 3H), 3.58 (s, 2H), 4.12 (q, J=7.2 Hz, 2H), 6.98-7.03 (m, 2H), 7.23-7.26 (m, 2H); $^{13}$CNMR (100 MHz, CDCl$_3$) δ 14.2, 40.5, 60.9, 115.3, 115.5, 129.8, 129.9, 130.8, 130.9, 160.8, 163.2, 171.5; HRMS (ESI) calcd. for $C_{10}H_{11}FNaO_2$ [M+Na]: 205.0635. found: 205.0634. The ethyl p-fluorophenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 59 mg product p-fluorophenylacetic acid was obtained by extraction with ethyl acetate, and the yield of hydrolysis was 91%.

Example 18

Preparation of p-Chlorophenylacetic Acid from p-Chlorotoluene and Ethanol

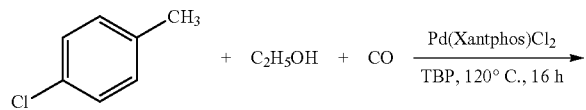

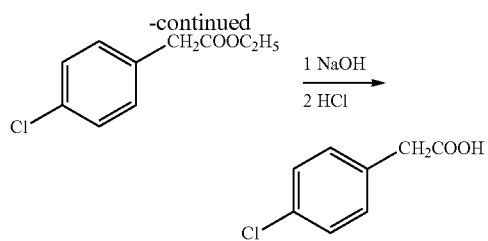

p-Chlorotoluene (1.89 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 89 mg ethyl p-chlorophenylacetate was obtained by column chromatography, in a yield of 90%. $^1$HNMR (400 MHz, CDCl$_3$) δ 1.23 (t, J=7.2 Hz, 3H), 3.57 (s, 2H), 4.12 (q, J=7.2 Hz, 2H), 7.19-7.23 (m, 2H), 7.27-7.30 (m, 2H); $^{13}$CNMR (100 MHz, CDCl$_3$) δ 14.2, 40.7, 61.0, 128.7, 130.7, 132.6, 133.0, 171.2; HRMS (ESI) calcd. for $C_{10}H_{11}ClNaO_2$ [M+Na]: 221.0340. found: 221.0342. The ethyl p-chlorophenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 75 mg product p-chlorophenylacetic acid was obtained by extraction with ethyl acetate, and the yield of hydrolysis was 98%.

Example 19

Preparation of p-Bromophenylacetic Acid from p-Bromotoluene and Ethanol

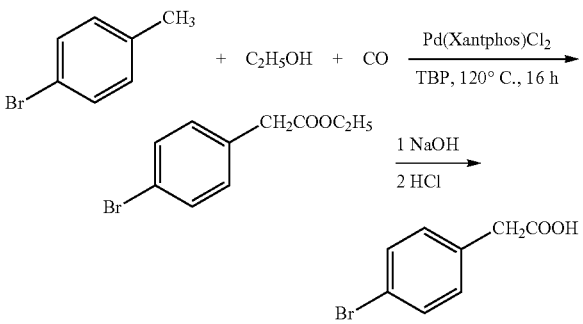

p-Bromotoluene (2.72 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 89 mg ethyl p-bromoacetate was obtained by column chromatography, in a yield of 73%. $^1$HNMR (400 MHz, CDCl$_3$) δ 1.23 (t, J=7.2 Hz, 3H), 3.56 (s, 2H), 4.12 (q, J=6.8 Hz, 2H), 7.15-7.17 (m, 2H), 7.43-7.45 (m, 2H); $^{13}$CNMR (100 MHz, CDCl$_3$) δ 14.2, 40.8, 61.0, 121.1, 131.0, 131.6, 133.1, 171.1; HRMS (ESI) calcd. for $C_{10}H_{11}BrNaO_2$ [M+Na]: 264.9835. found: 264.9837. The ethyl p-bromophenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 73 mg product p-bromophenylacetic acid was obtained by extraction with ethyl acetate, and the yield of hydrolysis was 93%.

Example 20

Preparation of o-Chlorophenylacetic Acid from o-Chlorotoluene and Ethanol

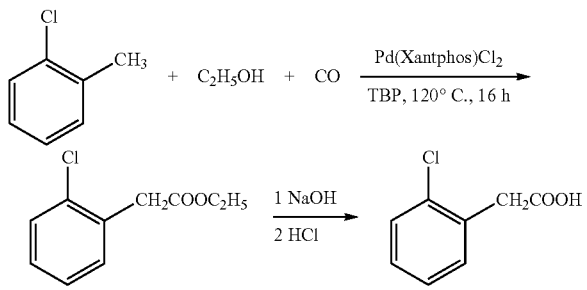

o-Chlorotoluene (1.89 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 82 mg ethyl o-chlorophenylacetate was obtained by column chromatography, in a yield of 83%. $^1$HNMR (400 MHz, CDCl$_3$) δ 1.24 (t, J=7.2 Hz, 3H), 3.77 (s, 2H), 4.15 (q, J=7.2 Hz, 2H), 7.21-7.24 (m, 2H), 7.28-7.30 (m, 1H), 7.36-7.40 (m, 1H); $^{13}$CNMR (100 MHz, CDCl$_3$) δ 14.2, 39.2, 61.0, 126.9, 128.6, 129.5, 131.4, 132.6, 134.6, 170.6; HRMS (ESI) calcd. for C$_{10}$H$_{11}$ClNaO$_2$ [M+Na]: 221.0340. found: 221.0343. The ethyl o-chlorophenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 66 mg product o-chlorophenylacetic acid was obtained by extraction with ethyl acetate, and the yield of hydrolysis was 94%.

Example 21

Preparation of m-Chlorophenylacetic Acid from m-Chlorotoluene and Ethanol

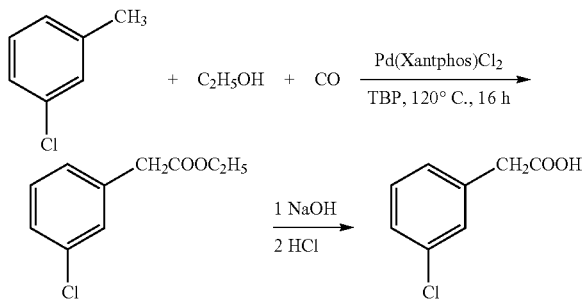

m-Chlorotoluene (1.89 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 82 mg ethyl m-chlorophenylacetate was obtained by column chromatography, in a yield of 83%. $^1$HNMR (400 MHz, CDCl$_3$) δ 1.24 (t, J=7.2 Hz, 3H), 3.58 (s, 2H), 4.13 (q, J=7.2 Hz, 2H), 7.15-7.18 (m, 1H), 7.24-7.26 (m, 1H), 7.29 (s, 1H); $^{13}$CNMR (100 MHz, CDCl$_3$) δ 14.2, 40.9, 61.1, 127.3, 127.5, 129.5, 129.8, 134.3, 135.9, 170.9; HRMS (ESI) calcd. for C$_{10}$H$_{11}$ClNaO$_2$ [M+Na]: 221.0340. found: 221.0342. The ethyl m-chlorophenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 64 mg product m-chlorophenylacetic acid was obtained by extraction with ethyl acetate, and the yield of hydrolysis was 91%.

Example 22

Preparation of 2,6-Dichlorophenylacetic Acid from 2,6-Dichlorotoluene and Ethanol

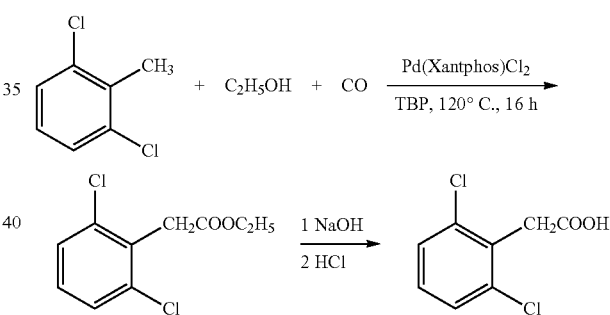

2,6-Dichlorotoluene (2.4 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 84 mg ethyl 2,6-dichlorophenylacetate was obtained by column chromatography, in a yield of 72%. $^1$HNMR (400 MHz, CDCl$_3$) δ 1.25 (t, J=7.2 Hz, 3H), 4.01 (s, 2H), 4.17 (q, J=7.2 Hz, 2H), 7.14-7.18 (m, 1H), 7.31-7.33 (m, 2H); $^{13}$CNMR (100 MHz, CDCl$_3$) δ 14.2, 36.8, 61.1, 128.0, 128.9, 131.4, 136.1, 169.5; HRMS (ESI) calcd. for C$_{10}$H$_{10}$Cl$_2$NaO$_2$ [M+Na]: 254.9950. found: 254.9949. The ethyl 2,6-dichlorophenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 71 mg product 2,6-dichlorophenylacetic acid was obtained by extraction with ethyl acetate, and the yield of hydrolysis was 95%.

Example 23

Preparation of 1-Naphthaleneacetic Acid from 1-Methylnaphthalene and Ethanol

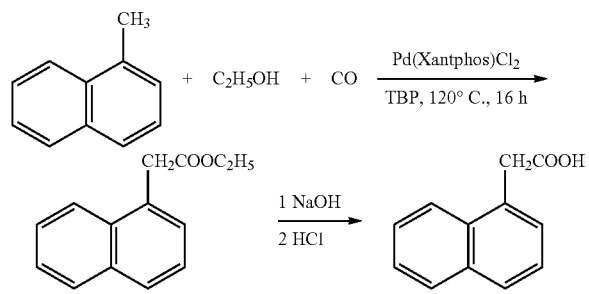

1-Methylnaphthalene (2.13 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 89 mg ethyl 1-naphthaleneacetate was obtained by column chromatography, in a yield of 83%. $^1$HNMR (400 MHz, CDCl$_3$) δ 1.20 (t, J=7.2 Hz, 3H), 4.06 (s, 2H), 4.12 (q, J=7.2 Hz, 2H), 7.39-7.55 (m, 4H), 7.78-7.80 (m, 1H), 7.84-7.85 (m, 1H), 7.99-8.01 (m, 1H); $^{13}$CNMR (100 MHz, CDCl$_3$) δ 14.2, 39.3, 60.9, 123.9, 125.5, 125.8, 126.3, 127.9, 128.0, 128.7, 130.7, 132.2, 133.9, 171.6; HRMS (ESI) calcd. for C$_{14}$H$_{14}$NaO$_2$ [M+Na]: 237.0886. found: 237.0889. The ethyl 1-naphthaleneacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 71 mg product 1-naphthaleneacetic acid was obtained by extraction with ethyl acetate, and the yield of hydrolysis was 92%.

Example 24

Preparation of 2-Naphthaleneacetic Acid from 2-Methylnaphthalene and Ethanol

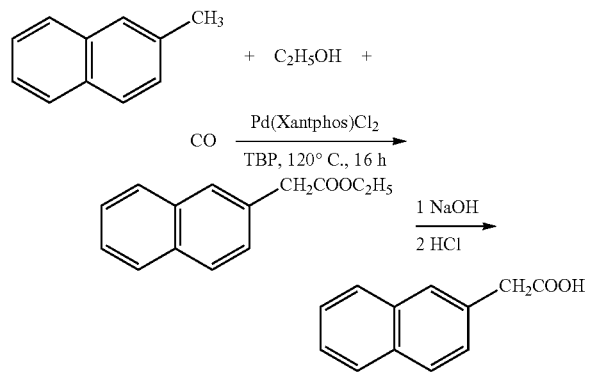

2-Methylnaphthalene (2.13 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 78 mg ethyl 2-naphthaleneacetate was obtained by column chromatography, in a yield of 73%. $^1$HNMR (400 MHz, CDCl$_3$) δ 1.24 (t, J=6.8 Hz, 3H), 3.78 (s, 2H), 4.14 (q, J=7.2 Hz, 2H), 7.41-7.49 (m, 3H), 7.73 (s, 1H), 7.79-7.83 (m, 3H); $^{13}$CNMR (100 MHz, CDCl$_3$) δ 14.2, 41.6, 60.9, 125.8, 126.1, 127.4, 127.7, 127.9, 128.2, 131.7, 132.5, 133.5, 171.6; HRMS (ESI) calcd. for C$_{14}$H$_{14}$NaO$_2$ [M+Na]: 237.0886. found: 237.0886. The ethyl 2-naphthaleneacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 62 mg product 2-naphthaleneacetic acid was obtained by extraction with ethyl acetate, and the yield of hydrolysis was 91%.

Example 25

Preparation of 2-Phenylpropanoic Acid from Ethylbenzene and Ethanol

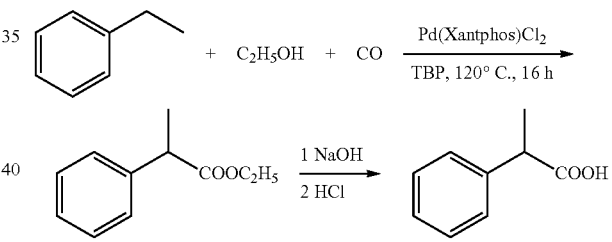

Ethylbenzene (1.59 g), ethanol (46 mg), di-tert-butyl peroxide (73 mg, 1 equivalent), and Pd(Xantphos)Cl$_2$ (3.8 mg, 1 mol %) were added into a reaction kettle, into which 30 atm carbon monoxide was introduced. The reaction was heated to 120° C., and stirred at this constant temperature for 16 h. After the reaction was completed, carbon monoxide was discharged, and 47 mg ethyl 2-phenylpropionate was obtained by column chromatography, in a yield of 53%. $^1$HNMR (400 MHz, CDCl$_3$) δ 1.17 (t, J=7.2 Hz, 3H), 1.48 (d, J=7.2 Hz, 3H), 3.67 (q, J=7.2 Hz, 2H), 4.07-4.18 (m, 1H), 7.21-7.26 (m, 1H), 7.27-7.33 (m, 4H); $^{13}$CNMR (100 MHz, CDCl$_3$) δ 14.1, 18.6, 45.6, 60.7, 127.1, 127.5, 128.6, 140.7, 174.5; HRMS (ESI) calcd. for C$_{11}$H$_{14}$NaO$_2$ [M+Na]: 201.0883. found: 201.0884. The ethyl 2-phenylpropionate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 37 mg product 2-phenylpropanoic acid was obtained by extraction with ethyl acetate, and the yield of hydrolysis was 93%.

Example 26

Preparation of Phenylacetic Acid from Toluene and Ethanol

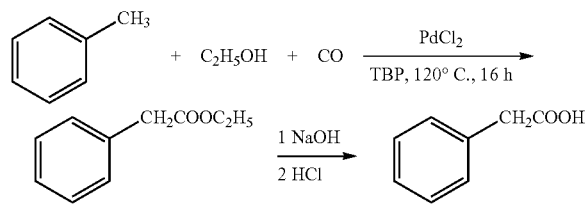

Toluene (1.38 g), ethanol (46 mg), di-tert-butyl peroxide (73 mg, 1 equivalent), and palladium chloride (0.9 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 47 mg ethyl phenylacetate was obtained by column chromatography, in a yield of 57%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 35 mg product phenylacetic acid was obtained by extraction with ethyl acetate, and the yield of hydrolysis was 90%.

Example 27

Preparation of Phenylacetic Acid from Toluene and Ethanol

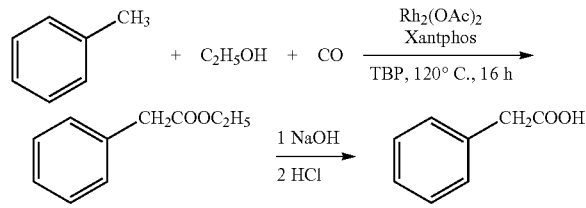

Toluene (1.38 g), ethanol (46 mg), di-tert-butyl peroxide (73 mg, 1 equivalent), rhodium acetate (0.8 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 63 mg ethyl phenylacetate was obtained by column chromatography, in a yield of 77%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 49 mg product phenylacetic acid was obtained by extraction with ethyl acetate, and the yield of hydrolysis was 94%.

Example 28

Preparation of Phenylacetic Acid from Toluene and Ethanol

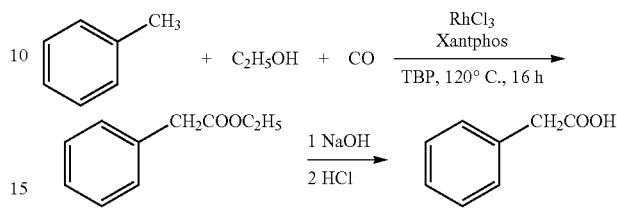

Toluene (1.38 g), ethanol (46 mg), di-tert-butyl peroxide (73 mg, 1 equivalent), rhodium trichloride (1.1 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 39 mg ethyl phenylacetate was obtained by column chromatography, in a yield of 48%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 29 mg product phenylacetic acid was obtained by extraction with ethyl acetate, and the yield of hydrolysis was 90%.

Example 29

Preparation of Phenylacetic Acid from Toluene and Ethanol

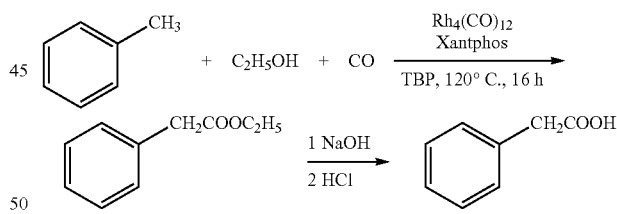

Toluene (1.38 g), ethanol (46 mg), di-tert-butyl peroxide (73 mg, 1 equivalent), carbonyl rhodium (0.9 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 29 mg ethyl phenylacetate was obtained by column chromatography, in a yield of 36%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 22 mg product phenylacetic acid was obtained by extraction with ethyl acetate, and the yield of hydrolysis was 91%.

Example 30

Preparation of Phenylacetic Acid from Toluene and Ethanol

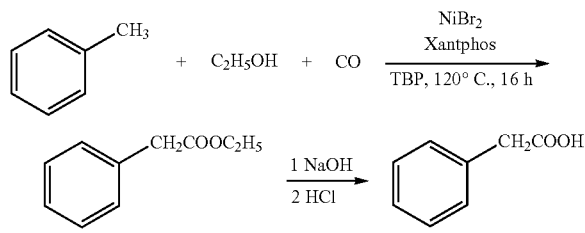

Toluene (1.38 g), ethanol (46 mg), di-tert-butyl peroxide (73 mg, 1 equivalent), nickel bromide (1.1 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 32 mg ethyl phenylacetate was obtained by column chromatography, in a yield of 39%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 25 mg product phenylacetic acid was obtained by extraction with ethyl acetate, and the yield of hydrolysis was 93%.

Example 31

Preparation of Phenylacetic Acid from Toluene and Ethanol

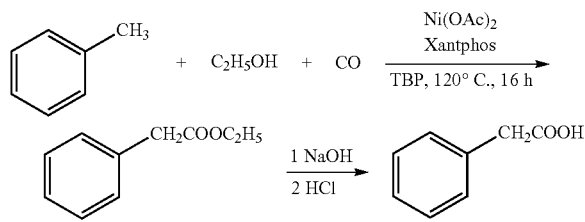

Toluene (1.38 g), ethanol (46 mg), di-tert-butyl peroxide (73 mg, 1 equivalent), nickel acetate (0.6 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 16 mg ethyl phenylacetate was obtained by column chromatography, in a yield of 20%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 12 mg product phenylacetic acid was obtained by extraction with ethyl acetate, and the yield of hydrolysis was 91%.

Example 32

Preparation of Phenylacetic Acid from Toluene and Ethanol

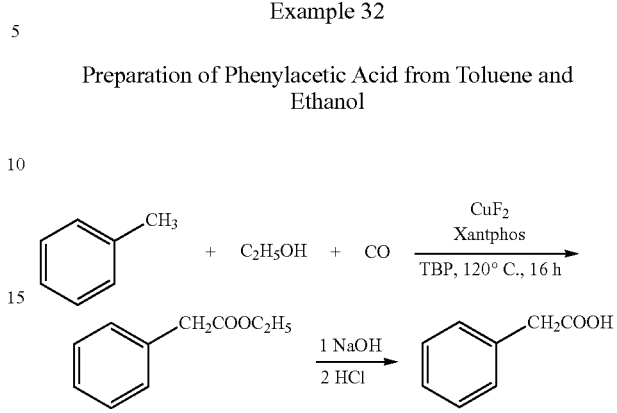

Toluene (1.38 g), ethanol (46 mg), di-tert-butyl peroxide (73 mg, 1 equivalent), copper fluoride (0.5 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 12 mg ethyl phenylacetate was obtained by column chromatography, in a yield of 15%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 9 mg product phenylacetic acid was obtained by extraction with ethyl acetate, and the yield of hydrolysis was 91%.

Example 33

Preparation of Phenylacetic Acid from Toluene and Ethanol

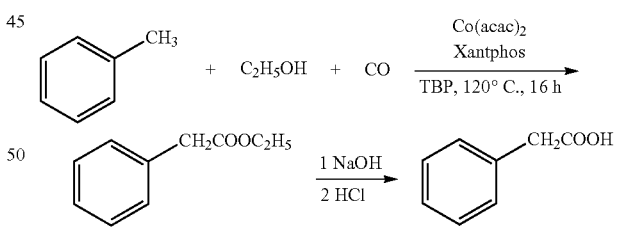

Toluene (1.38 g), ethanol (46 mg), di-tert-butyl peroxide (73 mg, 1 equivalent), cobalt acetylacetonate (1.3 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 14 mg ethyl phenylacetate was obtained by column chromatography, in a yield of 17%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 10 mg product phenylacetic acid was obtained by extraction with ethyl acetate, and the yield of hydrolysis was 93%.

Example 34

Preparation of Phenylacetic Acid from Toluene and Ethanol

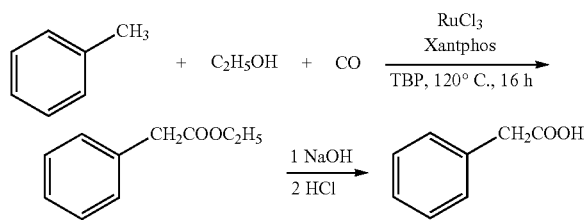

Toluene (1.38 g), ethanol (46 mg), di-tert-butyl peroxide (73 mg, 1 equivalent), ruthenium trichloride (1.1 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 13 mg ethyl phenylacetate was obtained by column chromatography, in a yield of 16%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 10 mg product phenylacetic acid was obtained by extraction with ethyl acetate, and the yield of hydrolysis was 92%.

Example 35

Preparation of Phenylacetic Acid from Toluene and Ethanol

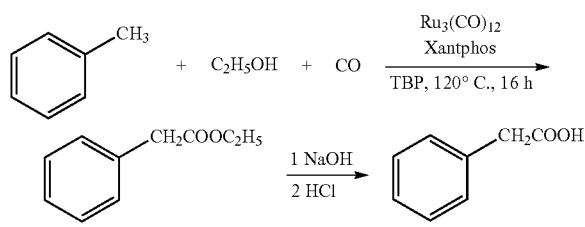

Toluene (1.38 g), ethanol (46 mg), di-tert-butyl peroxide (73 mg, 1 equivalent), carbonyl ruthenium (1.1 mg, 1 mol %), and Xantphos (2.9 mg) were added into a reaction kettle, into which 10 atm carbon monoxide was introduced. The reaction was heated to 120° C., and stirred at this constant temperature for 16 h. After the reaction was completed, carbon monoxide was discharged, and 22 mg ethyl phenylacetate was obtained by column chromatography, in a yield of 27%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 17 mg product phenylacetic acid was obtained by extraction with ethyl acetate, and the yield of hydrolysis was 93%.

Example 36

Preparation of Phenylacetic Acid from Toluene and Ethanol

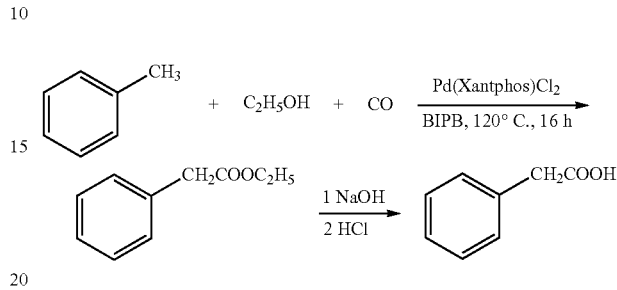

Toluene (1.38 g), ethanol (46 mg), bis(tert-butylperoxy) diisopropylbenzene (169 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 60 mg ethyl phenylacetate was obtained by column chromatography, in a yield of 73%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 46 mg product phenylacetic acid was obtained by extraction with ethyl acetate, and the yield of hydrolysis was 92%.

Example 37

Preparation of Phenylacetic Acid from Toluene and Ethanol

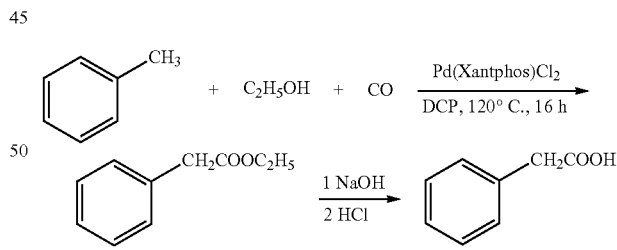

Toluene (1.38 g), ethanol (46 mg), diisopropylbenzene peroxide (135 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 35 mg ethyl phenylacetate was obtained by column chromatography, in a yield of 43%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 27 mg product phenylacetic acid was obtained by extraction with ethyl acetate, and the yield of hydrolysis was 93%.

Example 38

Preparation of Phenylacetic Acid from Toluene and Ethanol

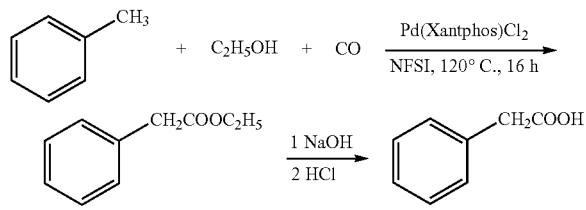

Toluene (1.38 g), ethanol (46 mg), N-fluorodibenzenesulfonamide (158 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 30 mg ethyl phenylacetate was obtained by column chromatography, in a yield of 37%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 23 mg product phenylacetic acid was obtained by extraction with ethyl acetate, and the yield of hydrolysis was 92%.

Example 39

Synthesis of Ibuprofen

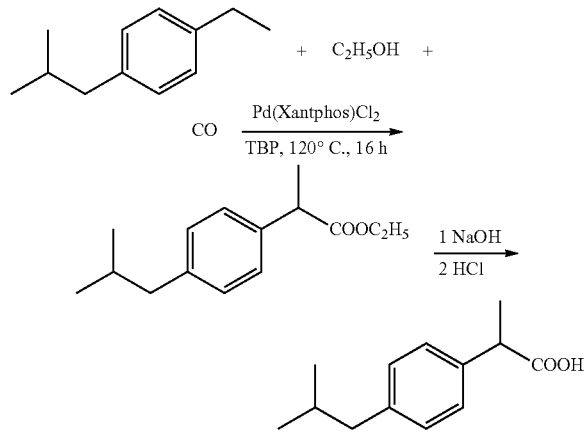

p-Isobutyl ethylbenzene (2.4 g), ethanol (46 mg), TBP (73 mg, 1 equivalent), and Pd(Xantphos)Cl$_2$ (3.8 mg, 1 mol %) were added into a reaction kettle, into which 10 atm carbon monoxide was introduced. The reaction was heated to 120° C., and stirred at this constant temperature for 16 h. After the reaction was completed, carbon monoxide was discharged, and 97 mg carbonylated ester product was obtained by column chromatography, in a yield of 83%. $^1$HNMR (400 MHz, CDCl$_3$) δ 0.91 (d, J=6.4 Hz, 6H), 1.29 (t, J=7.2 Hz, 3H), 1.61 (d, J=6.4 Hz, 3H), 1.82-1.84 (m, 1H), 2.43 (d, J=6.4 Hz, 2H), 3.78 (d, J=6.8 Hz, 2H), 4.21 (q, J=7.2 Hz, 2H), 7.05 (d, J=6.8 Hz, 2H), 7.24 (d, J=6.8 Hz, 2H); $^{13}$CNMR (100 MHz, CDCl$_3$) δ 13.7, 14.1, 22.8, 29.0, 40.2, 40.4, 44.5, 61.6, 128.8, 128.9, 132.2, 140.2, 173.7; HRMS (ESI) calcd. for C$_{15}$H$_{22}$NaO$_2$ [M+Na]: 257.1517. found: 257.1514. The ester product obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 83 mg product ibuprofen was obtained by extraction with ethyl acetate, and the yield of hydrolysis was 97%.

Example 40

Synthesis of Naproxen

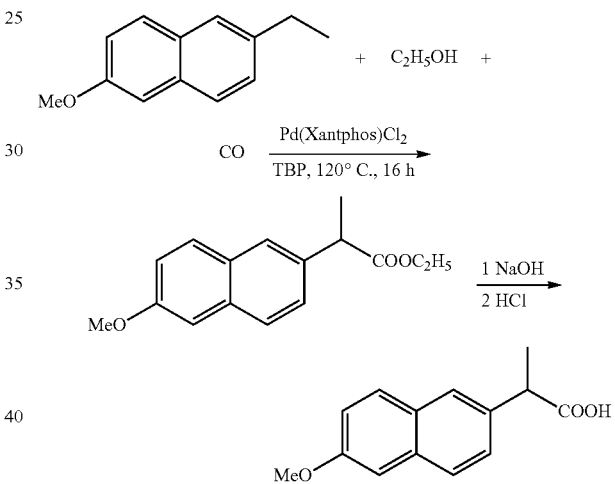

6-Methoxy-2-ethylnaphthalene (1.8 g), ethanol (46 mg), TBP (73 mg, 1 equivalent), Pd(Xantphos)Cl$_2$ (3.8 mg, 1 mol %), and benzene (1 mL) were added into a reaction kettle, into which 10 atm carbon monoxide was introduced. The reaction was heated to 120° C., and stirred at this constant temperature for 16 h. After the reaction was completed, carbon monoxide was discharged, and 102 mg carbonylated ester product was obtained by column chromatography, in a yield of 79%. $^1$HNMR (400 MHz, CDCl$_3$) δ 1.29 (t, J=7.2 Hz, 3H), 1.67 (d, J=6.4 Hz, 3H), 3.77-3.84 (m, 4H), 4.21 (q, J=7.2 Hz, 2H), 7.22-7.24 (m, 2H), 7.40-7.43 (m, 2H), 7.87-7.90 (m, 2H); $^{13}$CNMR (100 MHz, CDCl$_3$) δ13.7, 14.1, 40.8, 55.8, 61.6, 105.4, 126.1, 126.7, 128.5, 129.0, 129.4, 132.8, 133.0, 156.1, 173.7; HRMS (ESI) calcd. for C$_{16}$H$_{18}$NaO$_3$ [M+Na]: 281.1154. found: 281.1150. The ester product obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 84 mg product naproxen was obtained by extraction with ethyl acetate, and the yield of hydrolysis was 92%.

Example 41

Preparation of Phenylacetic Acid from Toluene and Ethanol

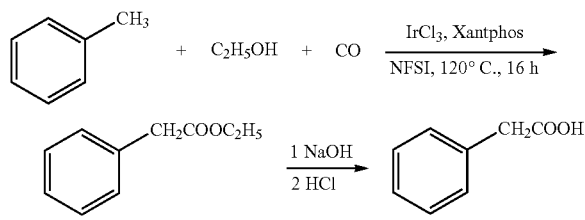

Toluene (1.38 g), ethanol (46 mg), di-tert-butyl peroxide (73 mg), iridium trichloride (1 mg, 1 mol %), and Xantphos (2.9 mg, 1 mol %) were added into a reaction kettle, into which 10 atm carbon monoxide was introduced. The reaction was heated to 120° C., and stirred at this constant temperature for 24 h. After the reaction was completed, carbon monoxide was discharged, and 43 mg ethyl phenylacetate was obtained by column chromatography, in a yield of 53%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 34 mg product phenylacetic acid was obtained by extraction with ethyl acetate, and the yield of hydrolysis was 96%.

Example 42

Preparation of 2-Phenylpropanoic Acid from Ethylbenzene and Ethanol

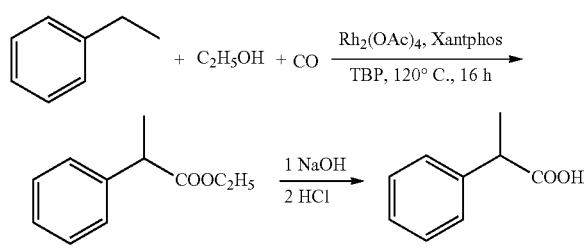

Ethylbenzene (1.59 g), ethanol (46 mg), di-tert-butyl peroxide (73 mg, 1 equivalent), $Rh_2(OAc)_4$ (1.1 mg, 0.5 mol %), and Xantphos (2.9 mg, 1 mol %) were added into a reaction kettle, into which 30 atm carbon monoxide was introduced. The reaction was heated to 120° C., and stirred at this constant temperature for 16 h. After the reaction was completed, carbon monoxide was discharged, and 77 mg ethyl 2-phenylpropionate was obtained by column chromatography, in a yield of 86%. The ethyl 2-phenylpropionate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 58 mg product 2-phenylpropanoic acid was obtained by extraction with ethyl acetate, and the yield of hydrolysis was 90%.

Example 43

Preparation of Phenylacetic Acid from Toluene and Ethanol

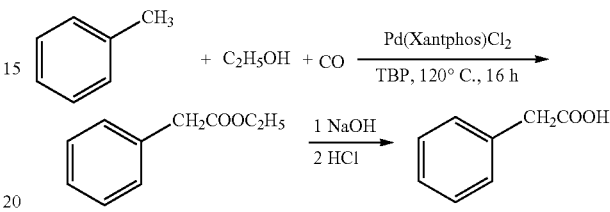

Toluene (18.4 g, 100 mmol), ethanol (1.84 g, 40 mmol), di-tert-butyl peroxide (5.84 g, 40 mmol), and Pd(Xantphos)$Cl_2$ (15.2 mg, 0.02 mmol) were added into a reaction kettle, into which 10 atm carbon monoxide was introduced. The reaction was heated to 120° C., and stirred at this constant temperature for 24 h. After the reaction was completed, carbon monoxide was discharged, and 4.2 g ethyl phenylacetate was obtained by column chromatography, in a yield of 64%, TON=1280. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 3.2 g product phenylacetic acid was obtained by extraction with ethyl acetate, and the yield of hydrolysis was 92%.

Example 44

Preparation of Phenylacetic Acid from Toluene and Ethanol

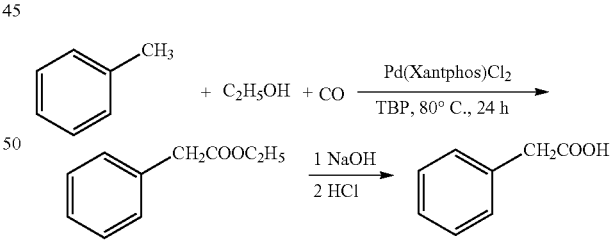

Toluene (1.38 g), ethanol (46 mg), di-tert-butyl peroxide (73 mg, 1 equivalent), and Pd(Xantphos)$Cl_2$ (3.8 mg, 1 mol %) were added into a reaction kettle, into which 10 atm carbon monoxide was introduced. The reaction was heated to 80° C., and stirred at this constant temperature for 24 h. After the reaction was completed, carbon monoxide was discharged, and 55 mg ethyl phenylacetate was obtained by column chromatography, in a yield of 67%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 39 mg product phenylacetic acid was obtained by extraction with ethyl acetate, and the yield of hydrolysis was 86%.

Example 45

Preparation of Phenylacetic Acid from Toluene and Ethanol

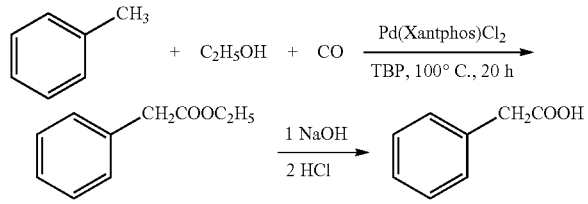

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 100° C., and stirred at this constant temperature for 20 h. After the reaction was completed, carbon monoxide was discharged, and 66 mg ethyl phenylacetate was obtained by column chromatography, in a yield of 80%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 49 mg product phenylacetic acid was obtained by extraction with ethyl acetate, and the yield of hydrolysis was 90%.

Example 46

Preparation of Phenylacetic Acid from Toluene and Ethanol

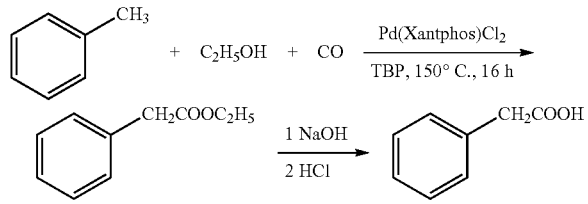

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 10 atm carbon monoxide was introduced. The reaction was heated to 150° C., and stirred at this constant temperature for 16 h. After the reaction was completed, carbon monoxide was discharged, and 60 mg ethyl phenylacetate was obtained by column chromatography, in a yield of 73%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 44 mg product phenylacetic acid was obtained by extraction with ethyl acetate, and the yield of hydrolysis was 89%.

Example 47

Preparation of Phenylacetic Acid from Toluene and Ethanol

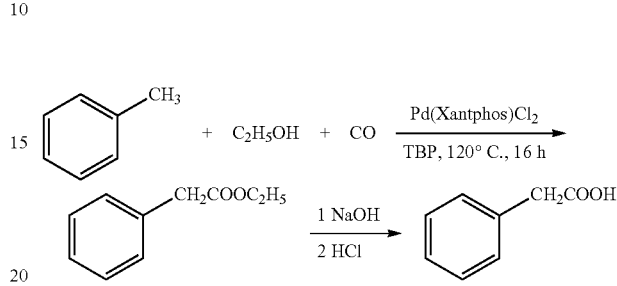

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 1 atm carbon monoxide was introduced. The reaction was heated to 120° C., and stirred at this constant temperature for 16 h. After the reaction was completed, carbon monoxide was discharged, and 43 mg ethyl phenylacetate was obtained by column chromatography, in a yield of 52%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 33 mg product phenylacetic acid was obtained by extraction with ethyl acetate, and the yield of hydrolysis was 93%.

Example 48

Preparation of Phenylacetic Acid from Toluene and Ethanol

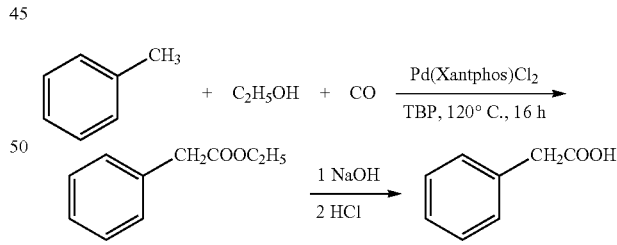

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 5 atm carbon monoxide was introduced. The reaction was heated to 120° C., and stirred at this constant temperature for 16 h. After the reaction was completed, carbon monoxide was discharged, and 61 mg ethyl phenylacetate was obtained by column chromatography, in a yield of 74%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 45 mg product phenylacetic acid was obtained by extraction with ethyl acetate, and the yield of hydrolysis was 86%.

Example 49

Preparation of Phenylacetic Acid from Toluene and Ethanol

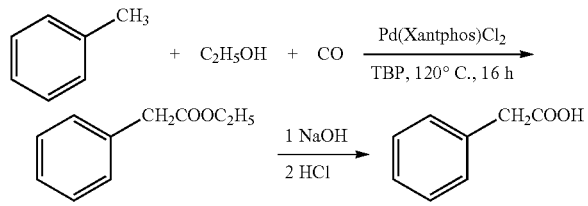

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 20 atm carbon monoxide was introduced. The reaction was heated to 120° C., and stirred at this constant temperature for 16 h. After the reaction was completed, carbon monoxide was discharged, and 71 mg ethyl phenylacetate was obtained by column chromatography, in a yield of 87%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 55 mg product phenylacetic acid was obtained by extraction with ethyl acetate, and the yield of hydrolysis was 93%.

Example 50

Preparation of Phenylacetic Acid from Toluene and Ethanol

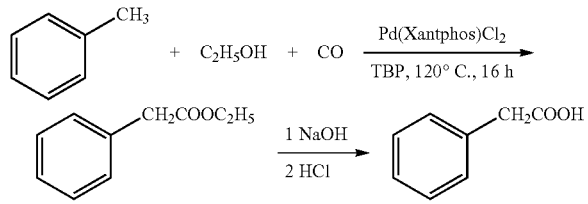

Toluene (1.38 g), ethanol (46 mg), di-tert-butyl peroxide (73 mg, 1 equivalent), and Pd(Xantphos)Cl$_2$ (3.8 mg, 1 mol %) were added into a reaction kettle, into which 50 atm carbon monoxide was introduced. The reaction was heated to 120° C., and stirred at this constant temperature for 16 h. After the reaction was completed, carbon monoxide was discharged, and 62 mg ethyl phenylacetate was obtained by column chromatography, in a yield of 76%. The ethyl phenylacetate obtained was dissolved in 1,4-dioxane. 6 N sodium hydroxide solution was added, and the reaction was heated to 60° C. After 2 h of reaction, the pH value was adjusted to 1 by adding 2 N hydrochloric acid. After removing the organic solvent under reduced pressure, 47 mg product phenylacetic acid was obtained by extraction with ethyl acetate, and the yield of hydrolysis was 91%.

The invention claimed is:
1. A preparation process comprising:
(a) reacting a compound of Formula (I)

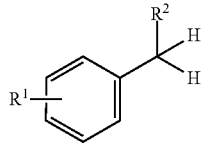

Formula (I)

with a compound represented by R$^3$OH in the presence of carbon monoxide, an oxidant, a transition metal catalyst, a ligand and a solvent to provide a compound of Formula (II):

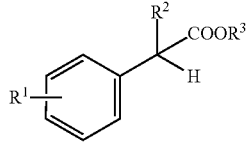

Formula (II)

(b) converting the compound of Formula (II) by hydrolysis to form a compound of Formula (III):

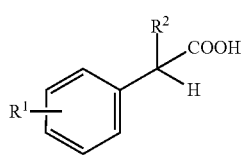

Formula (III)

wherein,
R$^1$ and R$^2$ are each independently selected from: hydrogen, linear or branched C$_1$-C$_{40}$ aliphatic hydrocarbyl, substituted or unsubstituted C$_6$-C$_{60}$ aryl group, linear or branched C$_1$-C$_{40}$ alkoxy, halogen, furanyl, furanyl substituted with 1-3 substituents selected from the group of consisting of C$_1$-C$_{40}$ alkyl, C$_1$-C$_{40}$ alkoxy, aryl, aryloxy and halogen; pyridinyl, pyridinyl substituted with 1-4 substituents selected from the group consisting of C$_1$-C$_{40}$ alkyl, C$_1$-C$_{40}$ alkoxy, aryl, aryloxy and halogen; hydroxyl, nitro, amino, linear or branched C$_1$-C$_{40}$ ester group linear or branched C$_1$-C$_{40}$ acyl and sulfonic acid group;
R$^3$ is linear or branched C$_1$-C$_{30}$ alkyl, benzyl or substituted benzyl.

2. The preparation process according to claim 1, characterized in that R$^1$ and R$^2$ are each independently a linear or branched C$_{1-4}$ alkyl.

3. The preparation process according to claim 1, characterized in that R$^1$ and R$^2$ are each independently selected from linear or branched C$_{1-4}$ alkoxy.

4. The preparation process according to claim 1, characterized in that R$^1$ and R$^2$ are each independently selected from phenyl, substituted phenyl, benzyl, substituted benzyl, 1-naphthyl, 2-naphthyl or substituted naphthyl.

5. The preparation process according to claim 1, characterized in that a precursor of the transition metal catalyst is one or more selected from: ruthenium-based metal catalyst precursors; ruthenium trichloride, dodecacarbonyltriruthenium;

rhodium-based metal catalyst precursors; palladium-based metal catalyst precursors; iridium-based metal catalyst precursors; cobalt-based metal catalyst precursors; nickel-based metal catalyst precursors; copper-based metal catalyst precursors.

6. The preparation process according to claim 1, characterized in that the oxidant is one or more selected from: peroxide oxidants; quinone type oxidants; fluorine type oxidants; oxygen; persulphates.

7. The preparation process according to claim 1, characterized in that the ligand is one or more selected from: phosphine ligands; and nitrogen ligands.

8. The preparation process according to claim 1, characterized in that the organic solvent is selected from benzene, nitromethane, toluene, trifluorotoluene, xylene, mesitylene, 1,4-dioxane, acetonitrile, propionitrile, dichloromethane, chloroform, carbon tetrachloride, 1,2-dichloroethane, ethyl ether, glycol dimethyl ether, methyl tert-butyl ether, methyl cyclopentyl ether, tetrahydrofuran, N,N-dimethylformamide, N,N-dimethylacetamide, dimethyl sulfoxide, or mixture thereof.

9. The preparation process according to claim 1 wherein converting the compound of Formula (II) by hydrolysis to form the compound of Formula (III) comprises hydrolyzing the compound of Formula (II) in the presence of an alkaline reagent followed by acidification.

10. The preparation process according to claim 9, characterized in that the hydrolyzing is performed in a pH range of 10-14.

11. The preparation process according to claim 1 wherein $R^1$ and $R^2$ is independently linear or branched $C_1$-$C_{20}$ aliphatic hydrocarbyl, substituted or unsubstituted $C_6$-$C_{20}$ aryl group, linear or branched $C_1$-$C_{20}$ alkoxy, linear or branched $C_1$-$C_6$ ester group or linear or branched $C_1$-$C_6$ acyl.

12. The preparation process according to claim 1 wherein $R^3$ is methyl, ethyl, propyl, isopropyl, butyl or isobutyl.

13. The preparation process according to claim 1 wherein, when $R^1$ or $R^2$ is furanyl with 1-3 substituents, the substituents are selected from the group consisting of $C_{1-4}$ alkyl, $C_{1-4}$ alkoxy, phenyl and phenoxy.

14. The preparation process according to claim 1 wherein, when $R^1$ or $R^2$ is pyridinyl with 1-4 substituents, the substituents are selected from the group consisting of $C_{1-4}$ alkyl, $C_{1-4}$ alkoxy, phenyl and phenoxy.

15. The preparation process according to claim 2 wherein $R^1$ and $R^2$ are each independently methyl, ethyl, propyl, isopropyl, butyl or isobutyl.

16. The preparation process according to claim 3 wherein $R^1$ and $R^2$ are each independently methoxy, ethoxy, propoxy, or butoxy.

17. The preparation process according to claim 5 wherein the precursor of the transition metal catalyst is one or more selected from: rhodium trichloride, rhodium acetate, dodecacarbonyltetrarhodium, tris(triphenylphosphinecarbonyl) rhodium hydride, triphenylphosphinecarbonyl rhodium acetylacetonate, vinyl rhodium chloride, palladium chloride, palladium on carbon, tetra(triphenylphosphine) palladium, di(triphenylphosphine) palladium dichloride, palladium acetate, palladium trifluoroacetate, benzonitrile palladium dichloride, acetonitrile palladium dichloride, palladium trifluoromethanesulfonate, iridium trichloride, carbonyl cobalt, cobalt chloride, cobalt bromide, cobalt acetylacetonate, nickel bromide, nickel acetate, nickel sulfate, nickel acetylacetonate, nickel chloride, copper fluoride, copper chloride, and copper acetylacetonate.

18. The preparation process according to claim 6 wherein the oxidant is di-tert-butyl peroxide, tert-butyl hydroperoxide, hydrogen peroxide, peroxyacetic acid, m-chloroperoxybenzoic acid, diisopropylbenzene peroxide, benzoyl peroxide, bis(tert-butylperoxy)diisopropylbenzene, p-benzoquinone, anthraquinone, tetrachlorobenzoquinone, tetramethyl-p-benzoquinone, dichlorodicyanobenzoquinone, N-fluorodibenzenesulfonamide, N-fluoropyridinium trifluoromethanesulfonate, N-fluoropyridinium tetrafluoroborate, potassium persulphate, sodium persulphate or potassium hydrogen persulphate.

19. The preparation process according to claim 7 wherein the ligand is Xantphos (4,5-bis(diphenylphosphino)-9,9-dimethylxanthene), BINAP (2,2'-bis(diphenylphosphino)-1,1'-binaphthyl), MeO-BIPHEP (2,2'-bis(diphenylphosphino)-6,6'-dimethoxy-1,1'-biphenyl), $PPh_3$ (triphenylphosphine), DPPF (1,1'-bis(diphenylphosphino)ferrocene), DPEphos (bis[(2-diphenylphosphino)phenyl]ether), pyridine, 2,2'-bipyridinyl, 2,2'-biquinolyl or 1,10-phenanthroline.

* * * * *